United States Patent [19]

Pinder

[11] Patent Number: 5,113,422
[45] Date of Patent: May 12, 1992

[54] RADIOGRAPHIC INTERPRETATION TRAINER/TEST SYSTEM

[75] Inventor: Hansel M. Pinder, Houston, Del.

[73] Assignee: The United States of America as represented by the Secretary of the Air Force, Washington, D.C.

[21] Appl. No.: 724,253

[22] Filed: Jul. 1, 1991

[51] Int. Cl.$^5$ .............................................. G01B 15/06
[52] U.S. Cl. ........................................ 378/58; 378/207
[58] Field of Search ....................... 378/58, 56, 54, 62, 378/207

[56] References Cited

U.S. PATENT DOCUMENTS

| | | | |
|---|---|---|---|
| 3,988,602 | 10/1976 | Gorsica, Jr. | 235/150.1 |
| 4,322,619 | 3/1982 | Nelson et al. | 250/323 |
| 4,610,157 | 9/1986 | Vicki et al. | 73/1 |
| 4,704,892 | 11/1987 | Tarnai | 378/207 |
| 4,727,251 | 2/1988 | Blincow et al. | 250/308 |
| 4,763,528 | 8/1988 | Bouami et al. | 73/799 |
| 4,819,256 | 4/1989 | Annis et al. | 378/87 |

Primary Examiner—Janice A. Howell
Assistant Examiner—Don Wong
Attorney, Agent, or Firm—Fredric L. Sinder; Donald J. Singer

[57] ABSTRACT

An improved system for training and testing radiographic interpreters is providing by cracking or otherwise causing structural defects in vinyl floor tiles which, when radiographic images of the floor tiles are made, produce images that accurately mimic the radiographic images of structural aluminum aircraft components. Other plastic, or aluminum, plates, called radiographic eliminating plates, are variously combined with the simulated aluminum sheets, called radiographic imaging plates, to produce a series of increasingly difficult to read radiographs for training and testing.

8 Claims, 1 Drawing Sheet

RADIOGRAPHIC INTERPRETATION TRAINER/TEST SYSTEM

RIGHTS OF THE GOVERNMENT

The invention described herein may be manufactured and used by or for the Government of the United States for all governmental purposes without the payment of any royalty.

BACKGROUND OF THE INVENTION

The present invention relates generally to radiographic structural crack detection methods, and more particularly to standardized radiographs of simulated aluminum test specimens for training and testing radiographic interpreters.

Radiographic structural crack detection uses X-ray or gamma irradiation of structural components, generally aluminum aircraft components, to produce radiographs that can be examined and interpreted to reveal developing cracks. Accurate interpretation of radiographs is an acquired skill. Successful training of radiographic interpreters depends on the knowledge, patience and sight of a trainer, and the number of example cracks identified during training. Experience, in number, quality and variety, are critical to the successful training of a radiographic interpreter.

Unfortunately, there are no standardized training aids or visual accuracy test programs for radiographic interpreters. Old radiographs of actual aircraft components found in the field to have defects are not even generally saved to be used as examples because they can be recycled for their silver, and for other reasons. Even if some individual trainers or training sites have been able to accumulate individual collections of example radiographs for training and testing trainees, these individual collections suffer from lack of variety and consistency between collections, and the limited number of different radiographs in each collection makes it impossible to give functionally equivalent tests to individual trainees without the dishonesty risks inherent with having to test all the students using the same radiographs.

Complete training will require a greater number and variety of sample radiographs than are now available. Attempts to deliberately crack aluminum structural components to create the variety and number of radiographs needed for training has not proved successful in practice. An example of the need for more test sample radiographs is that, with the few test samples available, it is often difficult to make clear to a student how and why a false positive is not, in fact, a real defect and how to avoid such false positives in the future.

Thus it is seen that there is a need for a greater number and wider variety of radiographs suitable for training and testing radiograph interpreters than are now available.

It is, therefore, a principal object of the present invention to provide a method for making simulated aluminum plates having simulated structural defects that produce radiographic images that accurately mimic the radiographic image of an actual aluminum structural component with a selected defect.

It is another object of the present invention to provide a method for simulating blurring and non-relevant indications on a radiograph to provide better training and testing.

It is yet another object of the present invention to provide a means for certification of radiographic interpreters.

It is a feature of the present invention that a great variety of different structure defects can be simulated.

It is another feature of the present invention that a system of incrementally differing example radiographic images can be made to facilitate training.

It is an advantage of the present invention that it allows rapid weeding out of radiographic interpreting trainees who do not have good contrast discrimination.

It is another advantage of the present invention is that it allows use of expired X-ray film, thus reducing cost and waste.

It is a further advantage of the present invention that the simulated aluminum sheets are inexpensive and straightforward to make and use.

These and other objects, features and advantages of the present invention will become apparent as the description of certain representative embodiments proceeds.

SUMMARY OF THE INVENTION

The present invention provides an accurate simulated aluminum aircraft component having a desired simulated defect that, when irradiated by x-rays or gamma radiation, accurately mimics the radiographic image of an actual aluminum structural component with a selected defect. The unique discovery of the present invention is that a conventional plastic vinyl composition floor tile, called here a radiographic imaging plate, has almost the same radiographic density as aluminum and, when hand cracked at different temperatures, will produce radiographic images that accurately mimic different types of fatigue cracks, and when cut, will accurately mimic hardness type cracks. Another discovery is that placing a second sheet of plastic or aluminum, called a radiographic eliminating plate, over or under the radiographic imaging plate allows the introduction of blurring or non-relevant indications for improved training and testing.

Accordingly, the present invention is directed to a method for making a training and testing radiograph that accurately mimics a radiograph of a hypothetical aluminum sheet having a preselected structural defect, comprising the steps of providing a sheet of stiff plastic, cracking the plastic sheet in a preselected manner to create a structural defect in the floor tile sheet, and making a radiograph of the cracked plastic sheet, whereby the radiographic image of the created structural defect in the plastic sheet radiograph mimics a radiographic image of the preselected structural defect in the hypothetical aluminum sheet. The method may, wherein the preselected structural defect is a fastener hole crack, further comprise the steps of drilling at least two spaced holes in the plastic sheet, and bending the plastic sheet about a line connecting two spaced holes in the plastic sheet until a crack connecting the two holes appears. The method may also, wherein the preselected structural defect is a fastener hole crack, further comprising the steps of drilling at least two spaced holes in the plastic sheet, providing a cracking tool, comprising a cylindrical rod and a tang attached to and extending radially from the rod, placing a hole in the plastic sheet over the rod and sliding the plastic sheet down the rod until the sheet contacts the tang, and bending the plastic sheet over the tang until a crack extending from the hole results. The stiff plastic sheet may be a sheet of vinyl composition floor tile. Before making the radiograph of the cracked plastic sheet, there may be placed over the cracked plastic sheet a second sheet of material to reduce the visibility of the crack on the resulting radiograph. The second sheet may also include marks that produce non-relevant indications on the resulting radiograph.

The present invention is also directed to a plate for radiographically simulating an aluminum structural component having a crack, comprising a sheet of vinyl composition floor tile, a plurality of drilled holes through the floor tile sheet, at least one crack in the floor tile sheet extending between two drilled holes.

DESCRIPTION OF THE DRAWINGS

The present invention will be more clearly understood from a reading of the following detailed description in conjunction with the accompanying drawings wherein.

DETAILED DESCRIPTION

Figure 1:
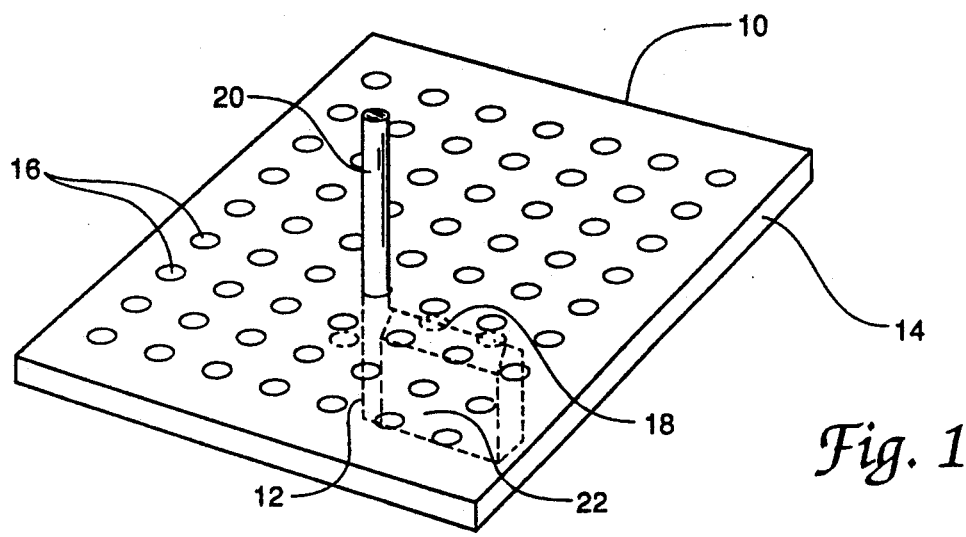
FIG. 1 is a perspective view of a stiff plastic radiographic imaging plate according to the teachings of the present invention being cracked over a cracking tool; and, FIG. 2 is a schematic perspective view of a radiograph being made of the cracked radiographic imaging plate of FIG. 1, also showing a radiographic eliminating plate according to the teachings of the present invention placed over the radiographic imaging plate.

Referring now to FIG. 1 of the drawings, there is shown a perspective view of a stiff plastic sheet 10 being hand cracked over a cracking tool 12 to make a radiographic imaging plate 14. Plastic sheet 10 is made of conventional vinyl composition floor tile. Various grades of Armstrong brand commercial floor tile have worked successfully, particularly Supreme Classic Vinyl Corlon, Imperial Texture Excelon and Classic Travertime Tiles, as described in the Armstrong 1983 Floors Product Information and Technical Data Brochure 9.23. These plastic floor tiles have almost the same radiographic density as aluminum. They produce, therefore, a radiographic image almost identical to aluminum.

Radiographic imaging plate 14 was made from a 12 inch square, 0.125 inch thick, vinyl composition floor tile. An 7.5 inch square area was marked off in the center of plate 14 and ten vertical and ten horizontal lines drawn 0.75 inches apart inside the inside square. To simulate fastener holes in an actual aluminum plate, 0.1875 inch diameter holes 16 were drilled at each line intersection. To simulate a crack 18 between fastener holes 16, imaging plate 14 was slid wear side down on shaft 20 of cracking tool 12 until hole 16 rested on a tang 22. Using a thumb and forefinger, imaging plate 14 was flexed over tang 22 until the plate cracked.

To simulate fatigue type cracks, radiographic imaging plate 14 should be first heated in an oven to about 95° F. to 110° F. To mimic the radiographic image of a stress corrosion type crack, or a integranular corrosion type crack, sheet 10 material should be heated in an oven to about 80° F. to 90° F. Cold type cracks can be simulated by cutting with a razor blade. The crack depth and type is generally controlled with temperature and pressure. The crack length is generally controlled with tang length, temperature and pressure.

To simulate an aluminum plate without fastener holes, a radiographic imaging plate without holes is bent over a tee tool until a crack results.

After the cracks are made, the radiographic imaging plate is exposed to make a radiograph to check the radiographic images. If the cracks are too vivid or too long, holes 16 can be drilled to a larger size.

Figure 2:
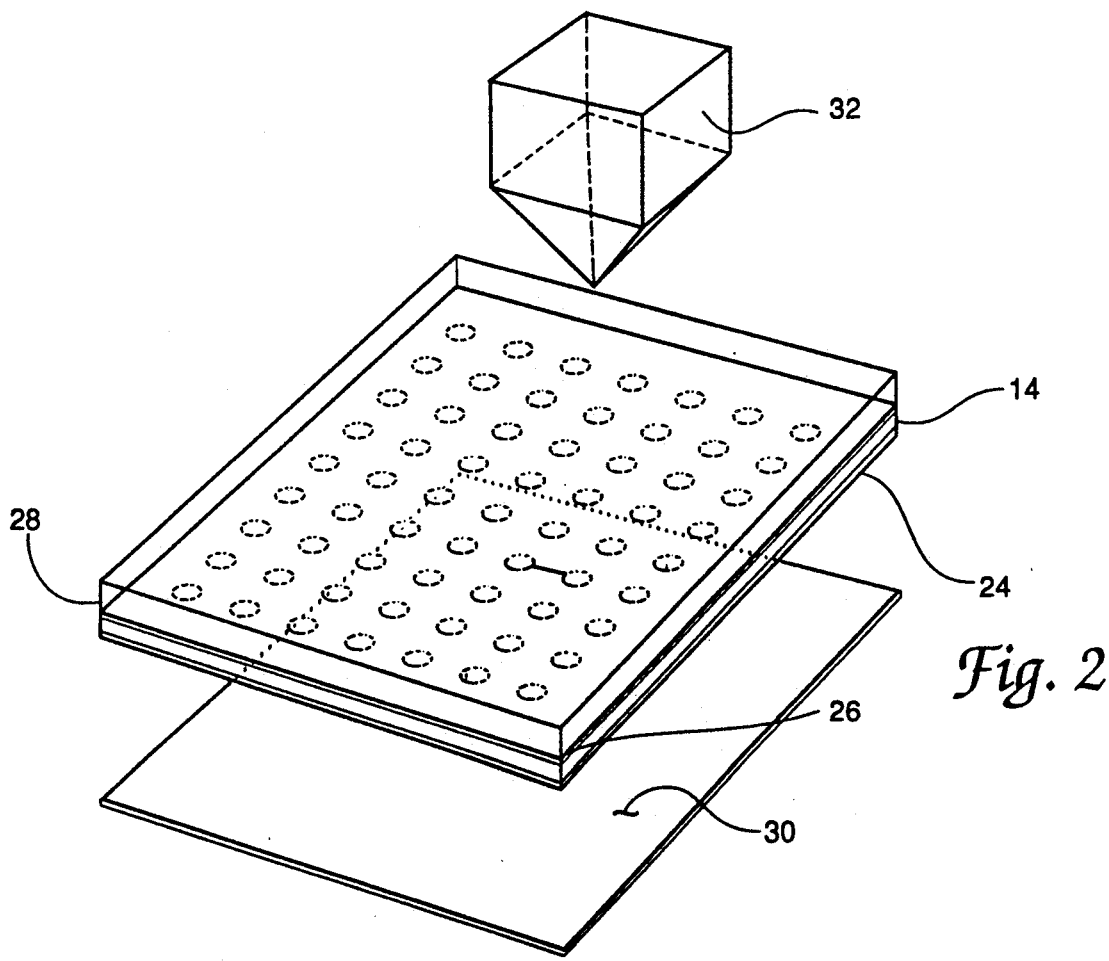

Next, a sheet of clear, stiff plastic 24, indicated in FIG. 2, is attached to the adhesive side of floor tile, or radiographic imaging plate, 14 as support. The thickness of radiographic imaging plate 14 is then reduced to 0.0625 inch or thinner by removing the wear side surface. This also removes any dings that may have resulting from the cracking step. A disk sander has worked well to perform this step. A second sheet of clear, stiff plastic 26 is then attached to the now ground down wear side of radiographic imaging plate 24. The two sheets of plastic help prevent radiographic imaging plate 14 from breaking.

FIG. 2 is a schematic perspective view of a radiograph 30 being made of cracked radiographic imaging plate 14. An X-ray head 32 provides X-rays for the exposure. In addition to the previously described protective plastic sheets 24 and 26, FIG. 2 also shows a radiographic eliminating plate 28. Radiographic eliminating plate 28 is a plate of aluminum, other metal, or plastic, and is the same size as radiographic imaging plate 14. Radiographic eliminating plate 28 serves to provide blurring to a resulting radiograph 30 so that a more realistic image for training and testing is provided. This is particularly important for testing contrast discrimination. Radiographic eliminating plate 28 may also be scratched or otherwise marked to provide non-relevant indications to resulting radiograph 30 to further refine training and testing. Eliminating plate 28 may be placed either over or under, or both, radiographic imaging plate 14. It will provide greater blurring when placed under radiographic imaging plate 14.

For training and testing, a variety of series of radiographs 30 should be prepared. First, a baseline radiograph with maximum crack visibility and minimum non-relevant indications should be made by making a clean radiograph of radiograph imaging plate 14 without any interfering radiographic eliminating plates 28, followed by other exposures of the same radiographic imaging plate with different combinations of radiographic imaging plate and radiographic eliminating plates to increasing blur the images and to add non-relevant indications. The radiographs should further be exposed in different densities, preferably divided into four radiographic density groups. The density groups preferably should be 0.5 to 1.4; 1.5–2.19; 2.20–2.90; and, 2.90–3.50. Then, other series of radiographs based on different baseline radiographic eliminating plates, with varying sizes and kinds of simulated cracks, should be made.

In use, radiographic interpreter trainees would start with more difficult to interpret radiographs and progress to baseline radiographs. The use of a baseline radiograph gives immediate positive feedback, especially where the trainee has available the baseline radiograph of any series to immediately detect mistakes and be better trained not only to detect defects, but also to avoid false positives.

The advantage of making radiographs in four different density groups, or families, the lower number families being less exposed and presenting lighter images, is that trainees quickly learn which family, from light to dark, they find easier to read. Then, in the future, they will know what exposure levels to use to improve their accuracy and efficiency. Unfortunately, the modern practice is to standardize at a density of 2.5, which sacrifices the increased accuracy available in the past by allowing individual interpreters more leeway over exposure densities.

The disclosed radiographic imaging plate and radiographic eliminating plate successfully demonstrates the use of a commonly available and easily workable material to simulate structural aluminum aircraft components having example structural defects for making otherwise unavailable sets of training and testing radiographs. Although the disclosed apparatus is specialized, its teachings will find application in other areas where training and testing sets are now unavailable due to high cost and other factors.

Radiographic images of cracks in structural aluminum components generally show up as dark lines. In medical X-rays, the search is generally for light lines, particular when searching for cancers in soft tissue. An example of extending the teachings of the present invention to medical X-rays would be to mill aluminum plates down to 0.001 inches, welding round welds onto the aluminum plate, and then machining or drilling small depth differences into the welds to create the light marks for training.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

I claim:

1. A method for making a training and testing radiograph that accurately mimics a radiograph of a hypothetical aluminum sheet having a preselected structural defect, comprising the steps of:
    (a) providing a sheet of plastic;
    (b) cracking the plastic sheet in a preselected manner to create a structural defect in the plastic sheet;
    (c) making a radiograph of the cracked plastic sheet, whereby the radiographic image of the treated structural defect in the plastic sheet radiograph mimics a radiographic image of the preselected structural defect in the hypothetical aluminum sheet.

2. The method for making a training and testing radiograph according to claim 1, wherein the preselected structural defect is a fastener hole crack, further comprising the steps of:
    (a) drilling at least two spaced holes in the plastic sheet; and,
    (b) bending the plastic sheet about a line connecting two spaced holes in the plastic sheet until a crack connecting the two holes appears.

3. The method for making a training and testing radiograph according to claim 1, wherein the preselected structural defect is a fastener hole crack, further comprising the steps of:
    (a) drilling at least two spaced holes in the plastic sheet;
    (b) providing a cracking tool, comprising:
        (i) a cylindrical rod; and
        (ii) a tang attached to and extending radially from the rod;
    (c) placing a hole in the plastic sheet over the rod and sliding the plastic sheet down the rod until the sheet contacts the tang;
    (d) bending the plastic sheet over the tang until a crack extending from the hole results.

4. The method for making a training and testing radiograph according to claim 1, wherein the plastic sheet is a sheet of vinyl composition floor tile.

5. The method for making a training and testing radiograph according to claim 1, further comprising the step of, before making the radiograph of the cracked plastic sheet, placing over the cracked plastic sheet a second sheet of material to reduce the visibility of the crack on the resulting radiograph.

6. The method for making a training and testing radiograph according to claim 5, wherein the second sheet includes marks that produce non-relevant indications on the resulting radiograph.

7. A plate for radiographically simulating an aluminum structural component having a crack, comprising:
    (a) a sheet of vinyl composition floor tile having a top and bottom;
    (b) a plurality of drilled holes through the floor tile sheet;
    (c) at least one crack in the floor tile sheet extending between two drilled holes;
    (d) a sheet of plastic attached to the bottom of the sheet of floor tile for support; and,
    (e) a sheet of plastic attached to the top of the sheet of floor tile for support.

8. A method for making a radiographic training and testing system, comprising the steps of:
    (a) providing a radiographic imaging plate made by steps comprising:
        (i) providing a first sheet of plastic; and,
        (ii) cracking the plastic sheet in a preselected manner to create a structural defect in the plastic sheet;
    (b) providing a plurality of radiographic eliminating plates made by steps comprising:
        (i) providing a second sheet made of one of plastic, aluminum or other metal; and,
        (ii) marking the second sheet so that its radiographic image will show one or both of blurs and structurally nonrelevant information; and,
    (c) making a series of radiographs beginning with a radiograph of the radiographic imaging plate alone, followed by radiographs of the radiographic imaging plate in combination with one or more radiographic eliminating plates so that the series of radiographs provide an increasingly more difficult-to-perceive image of the structural defect in the first sheet.

* * * * *

UNITED STATES PATENT AND TRADEMARK OFFICE
CERTIFICATE OF CORRECTION

PATENT NO.  : 5,113,422
DATED       : May 12, 1992
INVENTOR(S) : Hansel M. Pinder It is certified that error appears in the above-identified patent and that said Letters Patent is hereby corrected as shown below:

Column 5, line 46, (claim 1), "treated" should be --created--.

Signed and Sealed this

Fifth Day of October, 1993

*Attest:*

BRUCE LEHMAN

*Attesting Officer*    Commissioner of Patents and Trademarks